United States Patent [19]
Aghion

[11] Patent Number: 5,300,072
[45] Date of Patent: Apr. 5, 1994

[54] DEVICE FOR SECURING THE DISTAL END OF A SURGICAL PIN

[76] Inventor: Michael Aghion, 44, rue de l'Alma, F-92400 Courbevoie, France

[21] Appl. No.: 945,642

[22] PCT Filed: May 3, 1991

[86] PCT No.: PCT/FR91/00367
§ 371 Date: Nov. 4, 1992
§ 102(e) Date: Nov. 4, 1992

[87] PCT Pub. No.: WO91/16860
PCT Pub. Date: Nov. 14, 1991

[30] Foreign Application Priority Data
May 4, 1990 [FR] France .................. 90 05635

[51] Int. Cl.$^5$ ............................................. A61B 17/56
[52] U.S. Cl. ................................. 606/59; 606/96
[58] Field of Search .............. 606/59, 54, 55, 56, 606/53, 66, 72, 73, 101, 104, 96; 24/481, 482, 568, 569

[56] References Cited
U.S. PATENT DOCUMENTS

| | | | |
|---|---|---|---|
| 2,346,346 | 4/1944 | Anderson | 606/59 |
| 2,398,915 | 4/1946 | Bell . | |
| 3,916,748 | 11/1975 | Lee | 83/699 |
| 4,244,360 | 1/1981 | Dohogne | 606/59 |
| 4,271,832 | 6/1981 | Evans et al. | 606/59 |
| 4,312,101 | 1/1982 | Oetiker | 24/20 R |

FOREIGN PATENT DOCUMENTS

| | | |
|---|---|---|
| 1345527 | 10/1963 | France . |
| 2633822 | 1/1990 | France . |
| 952244 | 8/1982 | U.S.S.R. .................. 606/59 |

Primary Examiner—Stephen C. Pellegrino
Assistant Examiner—Guy V. Tucker
Attorney, Agent, or Firm—Young & Thompson

[57] ABSTRACT

A universal distal securement element for surgical pins of all utilized diameters, comprises a protective sphere provided with a bore for a pin and a clamping screw disposed in a tapped hole which opens into the bore. A crescent-shaped elastically deformable insert is disposed in the bore and the clamping screw bears against it. The deformable insert is deflected so that the insert has an internal cavity of progressively smaller cross section the deeper the screw is screwed into the tapped hole, thereby to permit clamping by the insert within the sphere of surgical pins of various diameters. The bore is circular in cross section and the crescent-shaped insert has edges that are disposed against sides of the bore remote from the screw, whereby upon screwing the screw progressively into the tapped hole, these edges approach each other. Alternatively, these edges overlie each other on the same side of the bore as the screw, whereby upon screwing the screw into the tapped hole, the overlapping edges slide against each other with an area of overlap that increases progressively as the screw is screwed into the hole.

4 Claims, 4 Drawing Sheets

DEVICE FOR SECURING THE DISTAL END OF A SURGICAL PIN

FIELD OF THE INVENTION

The invention relates to an element for universal distal securement, particularly for the external protection of the distal end of a pin adapted in particular for a finger of the hand but not exclusively for this latter.

BACKGROUND OF THE INVENTION

Distal pins used currently in surgery of the hand for the consolidation of the joints have diameters from 0.8 mm to 3 mm in steps of 0.2 mm to 0.5 mm. There exists, for protecting the end of this pin, in the external portion, a distal securement element in the form of a ball of plastic material resisting autoclaving. This ball is pierced diametrically by a hole permitting the passage of distal pins of similar diameters. For example, a distal securement element whose bore is 1.2 mm in diameter can receive pins that are 0.8 mm, 1.00 mm and 1.2 mm. For larger diameters, the exterior diameter of the ball will be greater. All these existing distal securement elements are pierced in the equatorial plane with a tapped hole in which the screwing action of a screw driver on a headless screw applies point pressure to the pin inserted in the element, such that this element will thus be fixed in rotation and in translation on the pin, thus preventing the latter from drifting relative to the hand, or relative to any other part of the body in which this pin might be implanted.

The distal securement element facilitates by its shape the treatment in dressing the wound, it thus makes it unnecessary for a surgeon to bend by 90 degrees the distal pin as was the case before this distal securement element.

To permit use of a securement element of this type for all diameters of existing pins, it has been proposed (French 2,633,822) to provide the securement element with orthogonal bores at the crossing of which opens the tapped hole of the clamping screw. This known arrangement is difficult to use by the physician, who must choose the bore corresponding to the pin which he has emplaced. Moreover, the unused bore constitutes a receptacle for organic products and organisms which are dangerous for the adjacent wound.

SUMMARY OF THE INVENTION

The present invention overcomes these drawbacks of the securement device known from French 2,633,822, thanks to a new device adaptable immediately to all diameters of existing pins which has no open bore after its emplacement.

To this end, the invention has for its object a universal distal securement element for surgical pins of all diameters used, of the type comprising a protective sphere provided with a bore for a pin and a clamping screw disposed in the tapped hole which opens into said bore, characterized in that it comprises an insert that is elastically deformable by means of said clamping screw and coming into contact with at least one generatrix of the pin to be protected, the deformable insert being in the shape of a crescent whose length of concave arc is approximately equal to the length of the circumference of the smallest usable pin, the radius before deformation corresponding to the radius of the largest diameter permissible pin.

The securement element according to the invention thus permits a simple and certain adaptation to all diameters of pins, with a single bore for the different pins. The elasticity of the insert causes it to return to disengagement position upon unscrewing the screw.

According to a preferred embodiment of the invention, the two ends of the deformable insert in the shape of a crescent are superposed in the active region of the clamping screw.

Preferably, said bore has a section greater than that of the pin of greatest section, the through bore being formed by a portion of the bore of circular section corresponding to that of the pin of greatest diameter, to which is connected the portion of an axially parallel bore whose section corresponds to that of the pin of smallest diameter. Preferably, the bore of largest diameter is closed at one end by a thin wall pierced in prolongation of the bore of smallest diameter, the bore of greatest diameter communicating with a diametrical recess opposed to the bore of smallest diameter and in the bottom of which is disposed said deformable insert in the form of a thin plate, the tapped hole opening into said bottom of the recess.

BRIEF DESCRIPTION OF THE DRAWINGS

The invention will be better understood from a reading of the following description given in reference to the accompanying drawing, in which.

DETAILED DESCRIPTION OF THE PREFERRED EMBODIMENT

Figure 1:
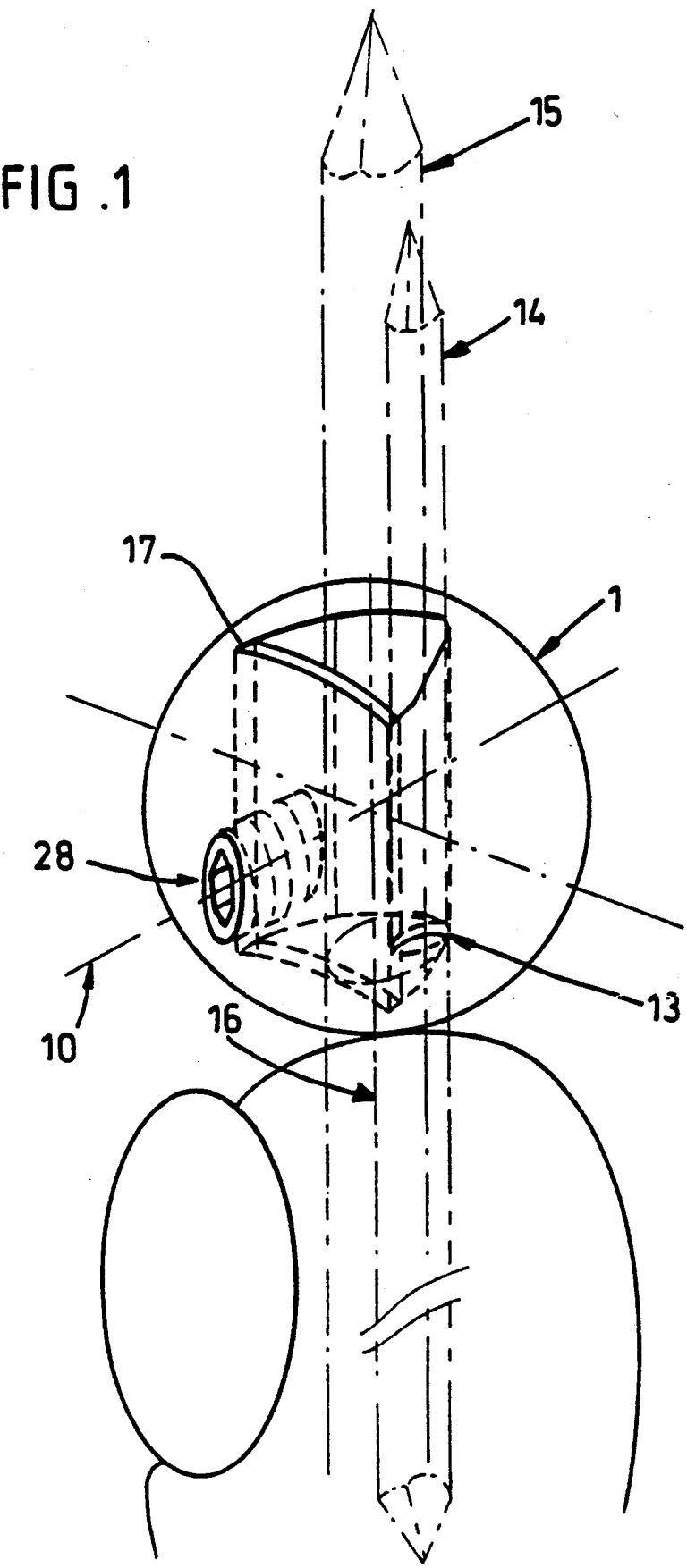
FIG. 1 is a schematic perspective view of a securement device according to one embodiment of the invention.
Figure 2:
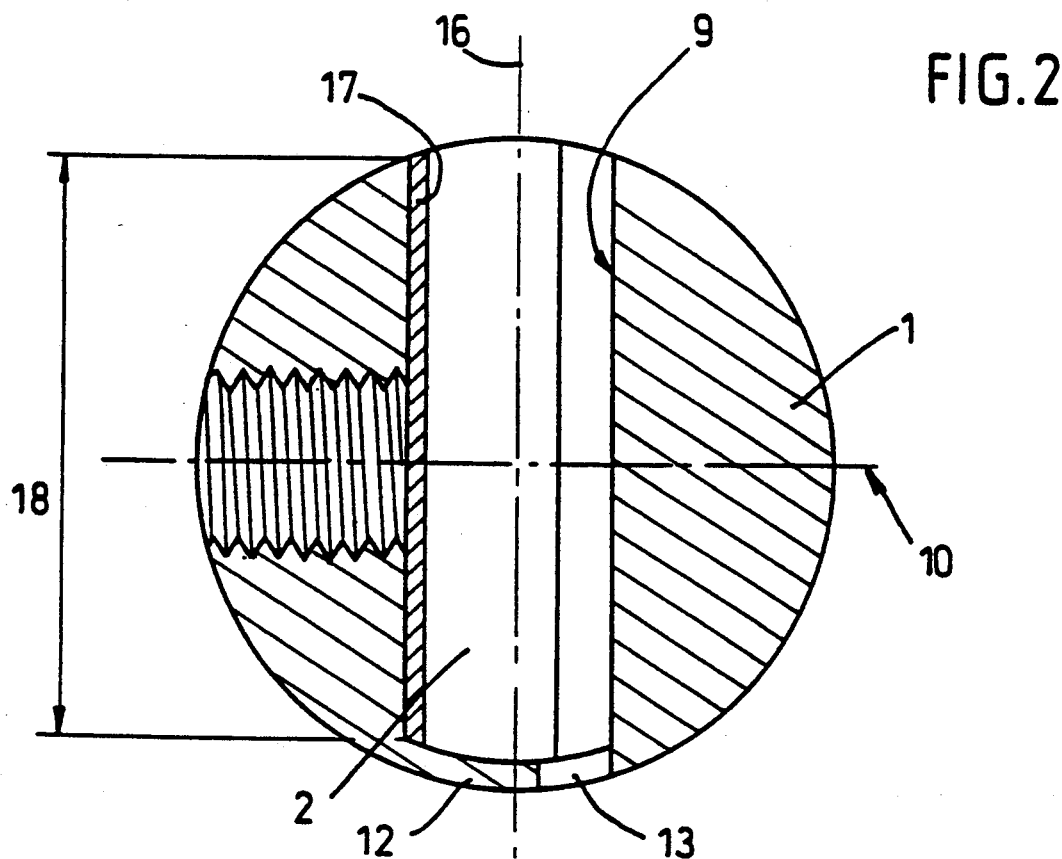
FIG. 2 is a diametrical sectional view passing through the axis of the bore of the device of FIG. 1.
Figure 3:
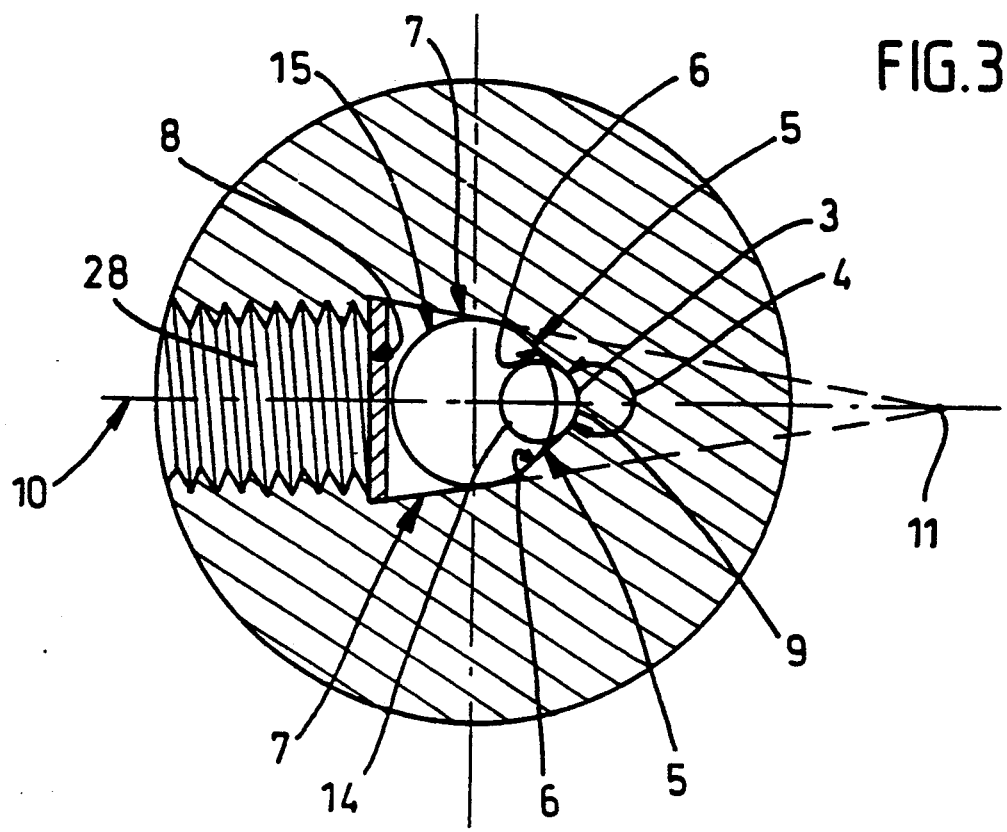
FIG. 3 is a diametrical cross sectional view at a right angle relative to FIG. 2.

Reference will be made first to FIGS. 1-3 which show the first embodiment of the invention.

The securement device comprises a sphere 1 provided with a blind recess 2 on axis 16 of sphere 1. Recess 2 is formed by a portion of a cylindrical bore 3 corresponding to the smallest diameter of permissible distal pin 14. The external generatrices 4 of the bore 3 are connected by two portions 5, to a portion of a cylindrical bore 6 whose section corresponds to the distal pins 15 of the largest diameter. The bore 6 is prolonged by two flats 7 providing, with a flat parallel to the medial generatrix 9 of the bore 3 and perpendicular to the diametrical plane 10 common to the bores 3 and 6, a recess. The two secant planes 7 intersect at 11 beyond the axis of the bore 3 so as to permit the passage of the largest diameter of distal pin 15. The part spherical web 12 which constitutes the closure of bore 2 is a thin wall pierced at the right side of bore 3 with a hole 13 corresponding to the smallest diameter of permissible distal pin 14.

In the previously described recess is disposed a blade 17 or insert of a small thickness, which is elastically deformable, this blade being in free contact with the flat 8. Its width is equal, with play, to the extent of flat 8 bounded by flats 7, the length of this blade being equal to the chord 18 resulting from the intersection of flats 7 and 8 less the thickness of the wall of the spherical cap 2. Its material is preferably stainless steel, but any other stainless material can be used.

The radial tapped hole disposed in the plane 10 opens into the recess and receives a screw 28 which, under the rotative action of a suitable screw driver, permits the permanent or temporary deformation (with resilient recovery) of the blade 17.

The universal distal securement device thus permits ensuring under excellent conditions the radial and transverse immobilization of sphere 1 on the distal pin thanks to linear contact along at least three generatrices 4 of the distal pin. The wedging against the flats 7 and the action of the screw 28 automatically cause the blade 17 to bend into V-shape.

The device prevents under certain pathological conditions the migration of human tissue into the space of crescent shape resulting in a hole which is too large with respect to the diameter of the distal pin, as would be produced with prior art elements. This drawback cannot arise with the invention, because the hole for passage of the pin is exactly adjusted by the introduction of the distal securement element on the latter.

Figure 4:
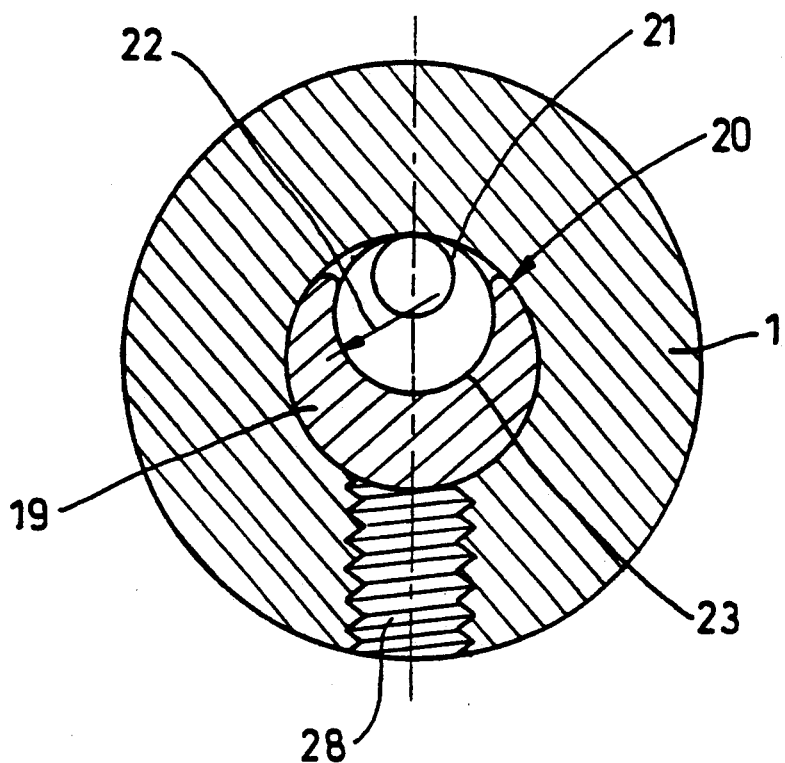
FIG. 4 is analogous to FIG. 3, showing a modification.

In the embodiment of FIG. 4, a single bore 20 of circular section corresponding to a diameter greater than the maximum diameter of permissible pin, receives a deformable insert 19 which, under the action of screw 28, will envelope the end of the pin to be protected. This deformable insert 19, in the form of a crescent, can be produced by drawing or extrusion. The length of the concave arc 23 of this crescent will be approximately equal to the length of the circumference of the smallest permissible pin 21. Its radius 22 before deformation will correspond to the radius of the greatest diameter of permissible pin in the sphere 1. By the pressure exerted by screw 28, the sliding of the generatrices of the deformable insert 19 in the form of a crescent along the generatrices of the hole 20 permits envelopment of all the generatrices of the end of the distal pin to be protected, thereby causing a very large number of generatrices to participate in the immobilization of the sphere on the distal pin.

Figure 6:
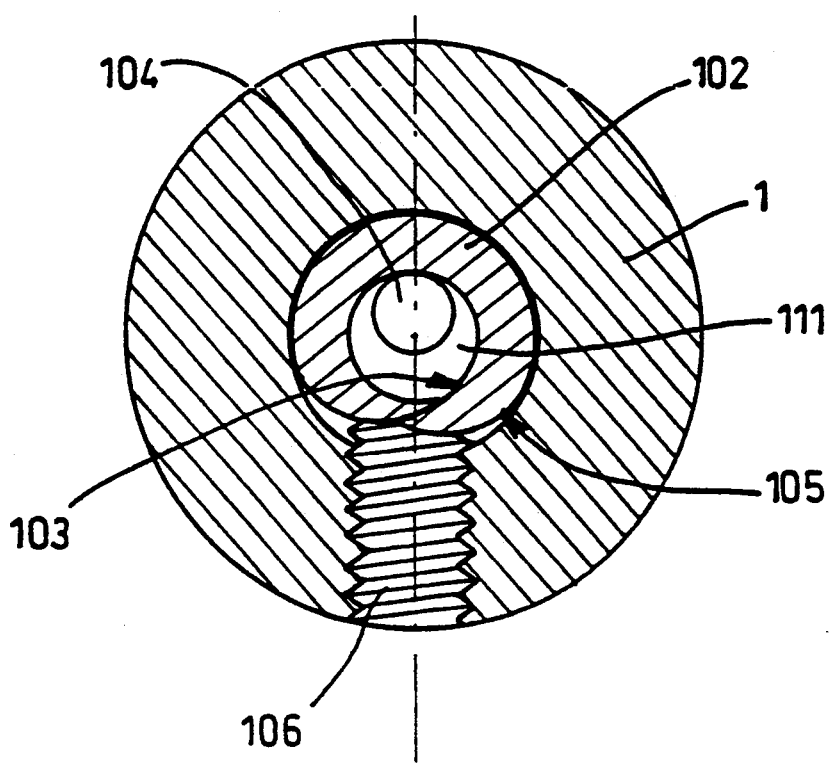
FIG. 6 is analogous to FIGS. 3 and 4, for the embodiment of FIG. 5.
Figure 5:
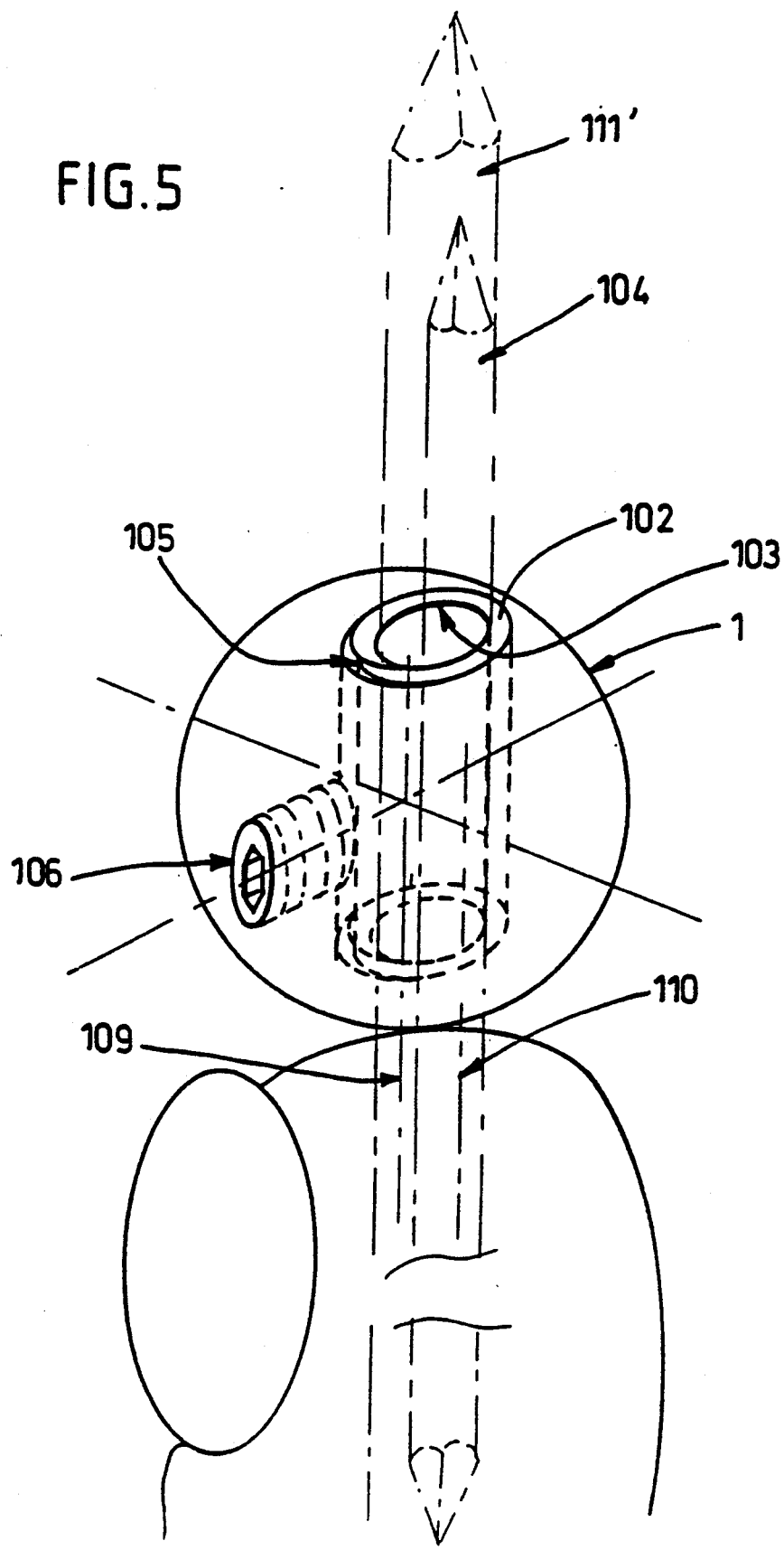
FIG. 5 is analogous to FIG. 1, for another embodiment of the invention.

In the preferred embodiment of FIGS. 5 and 6, better centering of the pin is ensured by causing a diameter 109 of the sphere 1 to coincide with the axis 110 of the pin to be protected, thanks to the sliding of the internal surface beginning at the beveled end of a strip 102 of constant thickness, against the external surface of the other beveled end of the same strip 102, in a recess 111 of the sphere 1.

The spiral overlapping of the strip 102, which is to say the internal surface 103 of strip 102 against external surface 105, and relative sliding of these two surfaces against each other, are effected by rotation of the screw 106 which, acting against the external surface 105 of the strip 102, forces the latter to reduce the length of the original internal circumference. The clamping screw 106 is provided with a thread whose pitch/diameter ratio is 8/100, in contrast to the thread of screws now used which is 6/100. Cessation of the clamping action of the screw permits, as in a spiral spring, the return of the strip to its original shape, thanks to the shape memory of its material.

The device permits centered clamping on pins 104 of small diameter as well as pins 111' of large diameter.

I claim:

1. In a universal distal securement element for surgical pins of all utilized diameters, comprising a protective sphere provided with a bore for a pin and a clamping screw disposed in a tapped hole which opens into said bore; the improvement comprising a crescent-shaped elastically deformable insert disposed in the bore and against which the clamping screw bears, and means deflecting the deformable insert so that the insert has an internal cavity of progressively smaller cross section the deeper the screw is screwed into said tapped hole thereby to permit clamping by said insert within said sphere of surgical pins of various diameters.

2. An element as claimed in claim 1, wherein said bore is circular in cross section and said crescent-shaped insert has edges that are disposed against sides of said bore remote from said screw, whereby upon screwing the screw progressively into the tapped hole, said edges approach each other.

3. An element as claimed in claim 1, wherein said crescent-shaped insert has edges that overlie each other on the same side of said bore as said screw, whereby upon screwing the screw into the tapped hole, said overlapping edges slide against each other with an area of overlap that increases progressively as said screw is screwed into the hole.

4. An element as claimed in claim 1, in combination with a set of pins of different diameters one of said pins being a pin of largest permissible diameter, said insert before deformation having an internal radius equal to the radius of said largest pin.

* * * * *